United States Patent [19]

Yoshikawa et al.

[11] Patent Number: 4,505,585
[45] Date of Patent: Mar. 19, 1985

[54] SYSTEM FOR DETECTING DEFECTS ON AN OPTICAL SURFACE

[75] Inventors: Shoji Yoshikawa; Ken Ohshima; Hiroshi Kodama; Kunio Yamamiya; Masaharu Sakamoto; Kiichi Kato, all of Tokyo, Japan

[73] Assignee: Olympus Optical Co., Ltd., Tokyo, Japan

[21] Appl. No.: 362,680

[22] Filed: Mar. 29, 1982

[30] Foreign Application Priority Data

Mar. 31, 1981 [JP] Japan .................................. 56-48006

[51] Int. Cl.$^3$ ..................... G01N 21/32; G06F 15/20; G01B 11/30
[52] U.S. Cl. .................................. 356/237; 73/432 L; 356/371; 364/507; 364/525
[58] Field of Search ............... 364/468, 474, 517, 524, 364/525, 550, 551, 556, 507, 562; 73/432 L; 356/371, 237

[56] References Cited

U.S. PATENT DOCUMENTS

| | | | |
|---|---|---|---|
| 3,302,786 | 2/1967 | Conrad | 73/432 L |
| 3,670,153 | 6/1972 | Rempert et al. | 364/468 |
| 4,177,539 | 9/1978 | Bell et al. | 364/468 |
| 4,247,203 | 1/1981 | Levy et al. | 356/398 |
| 4,314,763 | 2/1982 | Steigmeier et al. | 356/237 |
| 4,332,477 | 6/1982 | Sato | 356/171 |
| 4,347,001 | 8/1982 | Levy et al. | 356/398 |
| 4,353,650 | 10/1982 | Summargren | 356/171 |
| 4,448,532 | 5/1984 | Joseph et al. | 356/237 |

Primary Examiner—James D. Thomas
Assistant Examiner—Dale M. Shaw
Attorney, Agent, or Firm—Frishauf, Holtz, Goodman and Woodward

[57] ABSTRACT

In a system for detecting defects on an optical surface, a disk to be inspected is mounted on a turntable, and is attracted on the surface of the turntable. On the disk is provided an optical head having an objective lens located at its focal point on the surface of the disk. A laser beam emitted from a laser unit is projected through the optical head onto the disk, is reflected on the disk, and is then directed through the optical head to a photo detector. The optical head is moved in the radial direction of the disk as the turntable is rotated, and the disk is helically scanned by the laser beam. Only a defect signal is extracted from an electrical signal generated from the photo detector in a defect signal generator. The defect signal is compared in a data processing unit, and is converted to defect information of different size. When it is judged that a prescribed region on the surface of the disk is scanned by a position signal from a position sensor for detecting the position of the optical head, the data processing unit generates an address, and the defect information is stored in each size in specific assigned locations of the RAM. The defect information thus stored is displayed on a CRT or is printed out by a printer.

9 Claims, 12 Drawing Figures

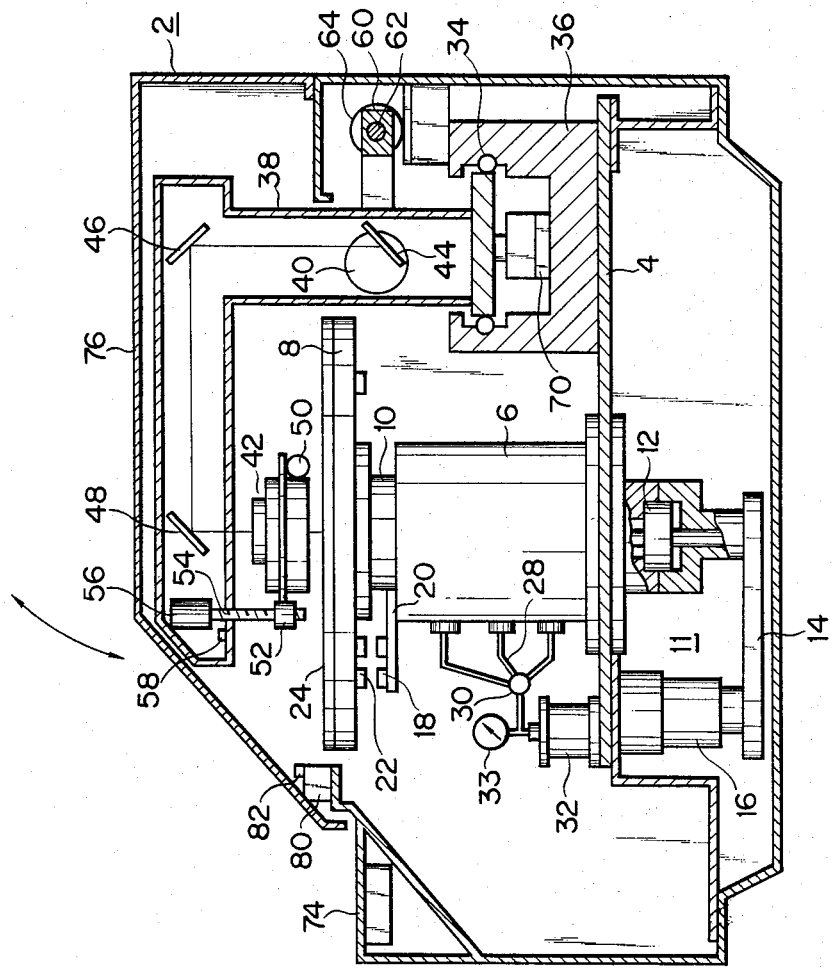
F I G. 1

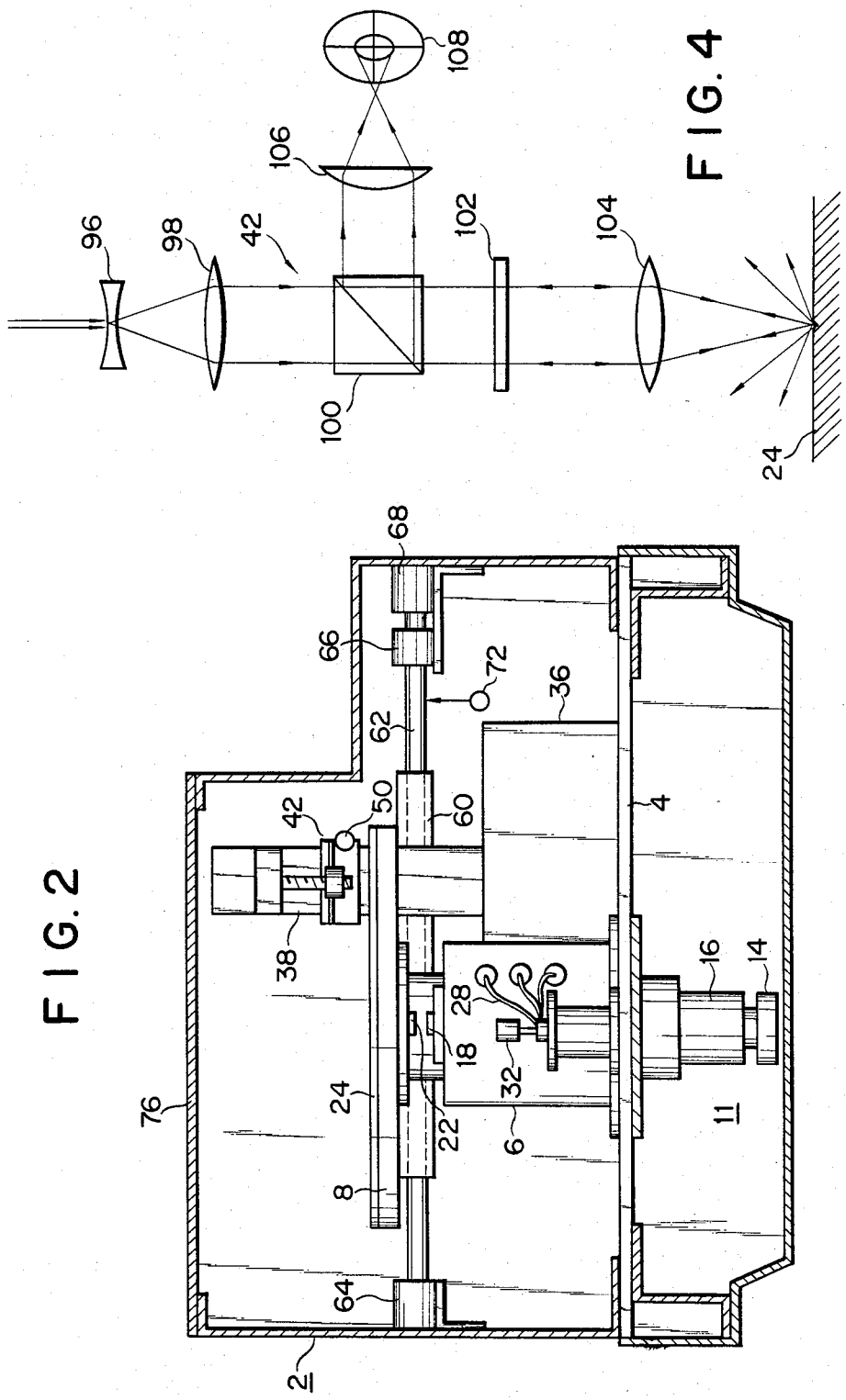

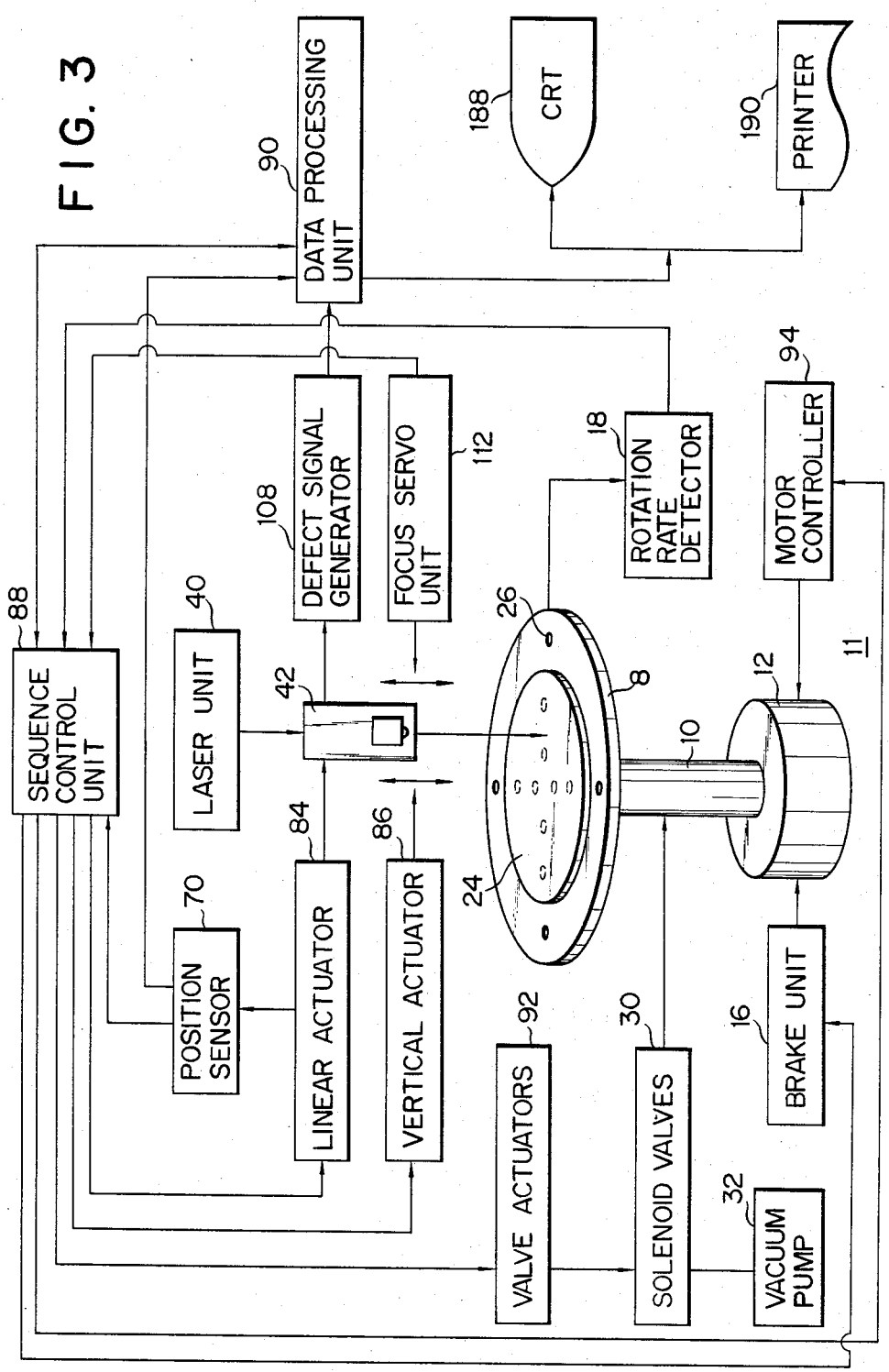

F I G. 10
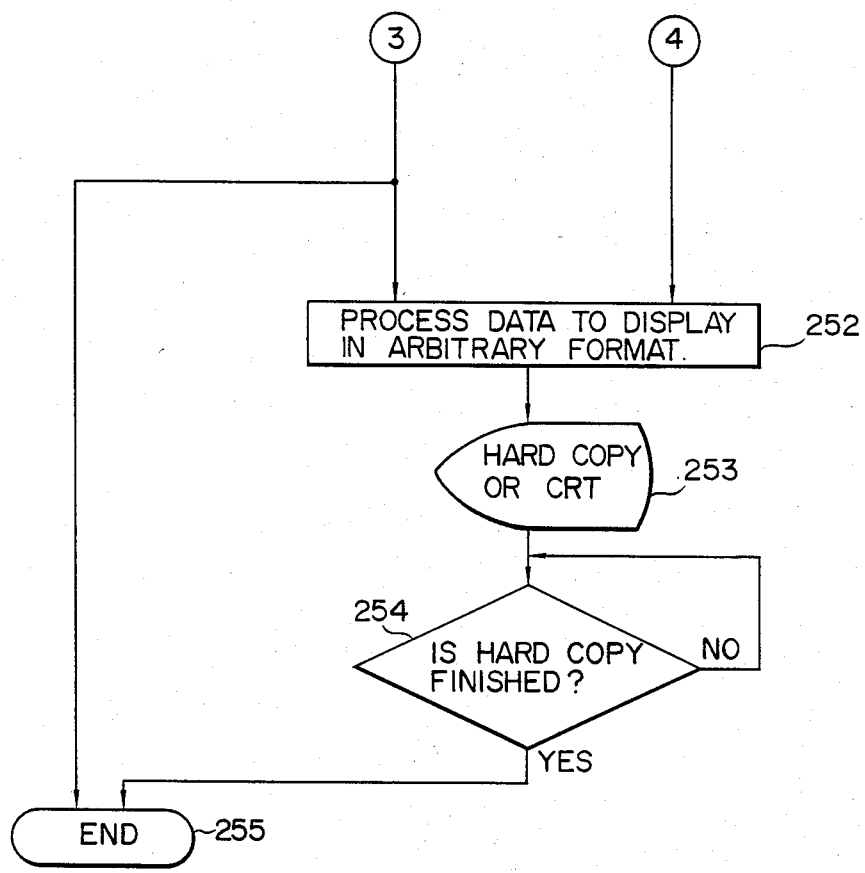

| | $a_1-a_0$ | $a_2-a_1$ | $a_3-a_2$ | ......... | $a_{n-2}-a_{n-3}$ | $a_{n-1}-a_{n-2}$ | $a_n-a_{n-1}$ |
|---|---|---|---|---|---|---|---|
| L | | | | ......... | | | |
| M | | | | ......... | | | |
| S | | | | ......... | | | |

SYSTEM FOR DETECTING DEFECTS ON AN OPTICAL SURFACE

BACKGROUND OF THE INVENTION

This invention relates to a system for detecting defects on an optical surface and, more particularly, to a system for detecting surface defects such as scratches, cracks, pin holes or the like on the optical surface of an object such as a semiconductor wafer or the original disk of an optical video disk on which no information is recorded.

It is generally required that the surface of a semiconductor wafer or of an original disk of an optical video disk on which no information is recorded should be optically flat. Accordingly, the surfaces of these wafers and disks are polished to become optically flat. It is then necessary to inspect whether the surfaces of these wafers and disks are reliably optically flat. In the conventional surface inspection, the surface of an object to be inspected is illuminated, is photographed by a TV pick-up tube or the like, and an enlarged, image is visually inspected by a person to discover any defects.

Since it is necessary to provide a TV camera having a high resolution in the human visual inspection technique, this inspection technique incorporates problems, e.g., personal differences, fatigue and so forth, and a skillful inspector is required. This conventional inspection technique is inefficient, unreliable, and it is difficult to quantify defects. It is also difficult to reliably detect fine surface defects.

SUMMARY OF THE INVENTION

It is an object of the present invention to provide a system for detecting defects on the surface of an object with high reliability and efficiency.

According to the present invention, there is provided a system for detecting defects on an optically flat surface of an object which comprises: a turntable having a surface on which the object is mounted, means for rotating the turntable, means for generating a laser beam, an optical unit for projecting a laser beam onto the surface of the object and directing the laser beam reflected from the surface of the object in a predetermined direction, means for converting the reflected laser beam directed from the optical unit into a photo-electric signal, means for moving the optical unit relative to the rotating turntable in a radial direction of the turntable, means for generating a position signal depending on the position of the object onto which laser beam is projected, means for generating a defect signal from the photo-electric signal, means for generating addresses from the position signal, which includes memory having a number of memory locations for storing the defect signals in the locations designated by the generated addresses, and means for activating the aforementioned respective means in a predetermined sequence.

BRIEF DESCRIPTION OF THE DRAWINGS

FIG. 1 is a longitudinal sectional side view schematically showing one preferred embodiment of a system for detecting defects on an optical surface according to the present invention;

FIG. 2 is a longitudinal sectional front view schematically showing the system shown in FIG. 1;

FIG. 3 is a block diagram of the system shown in FIG. 1;

FIG. 4 is an optical arrangement showing the optical unit shown in FIG. 1;

FIGS. 7 through 10 are flowcharts showing the operational sequence of the system shown in FIGS. 1 to 4;

DETAILED DESCRIPTION OF THE PREFERRED EMBODIMENTS

Figure 5:
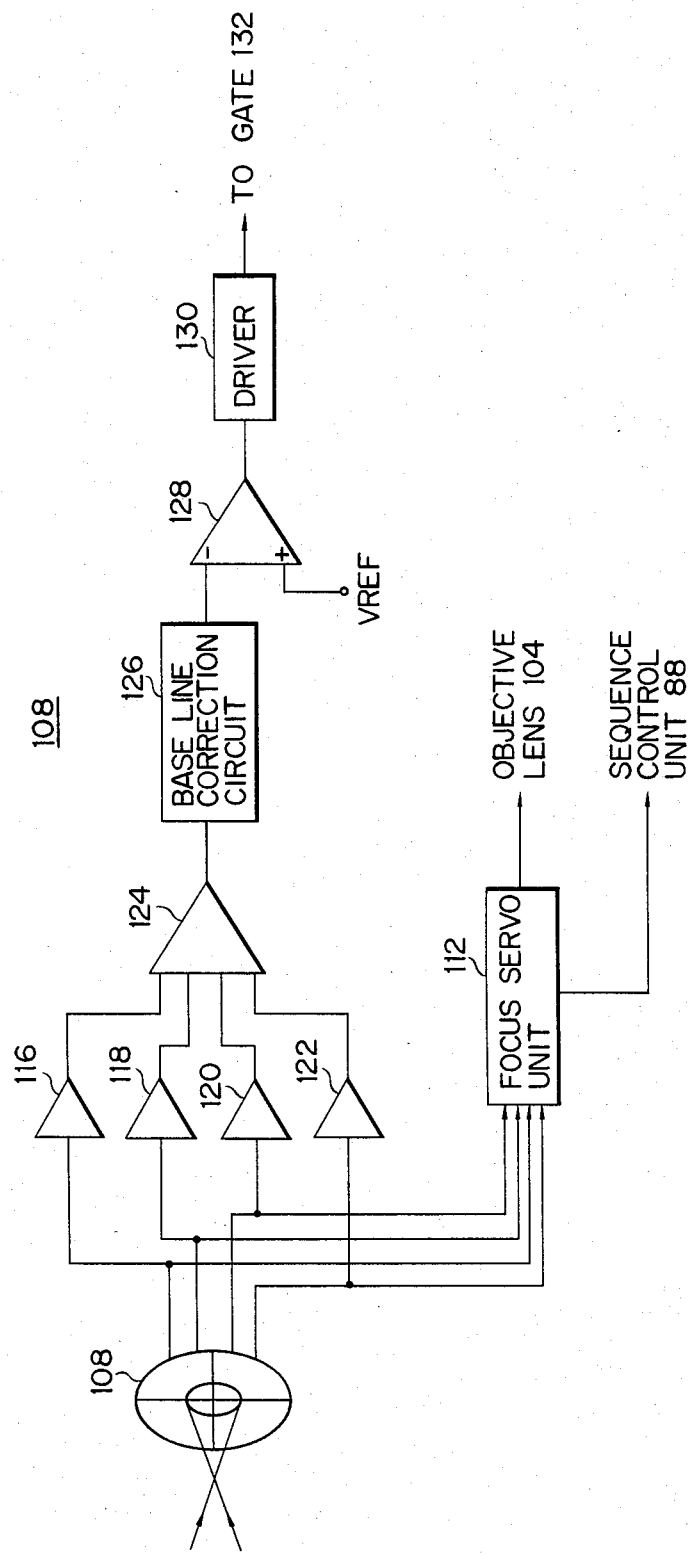
FIG. 5 is a block diagram showing the defect signal generator shown in FIG. 3.

FIGS. 1 and FIG. 2, are longitudinal sectional side and front views schematically illustrating the system for detecting defects on a surface of an object according to one preferred embodiment of the present invention. In this system, a bearing 6 is mounted on a base 4 which is fixed in a housing 2, a turntable 8 is provided on the bearing 6, a turntable shaft 10 is coupled with the turntable 8 and hence the turntable 8 is rotatably supported by the bearing 6.

A turntable driving mechanism 11 for rotating the turntable 8 is provided in the lower section of the housing 2. In the driving mechanism 11, the shaft of the motor 12 is connected to the turntable shaft 10, and a timing pulley or belt is connected between a brake unit 16 and the motor shaft of the motor 12. A rotation rate detector 18 for detecting the rotating rate of the turntable 8 rotated by the motor 12 is provided on a plate 20 extending from the bearing 6 under the back or bottom surface of the turntable 8. A member 22 to be detected by the rotation rate detector 18 is provided on the circumference of the bottom surface of the turntable 8. When the rotation rate detector 18 employs a photo diode and a light emitting diode, the member 22 to be detected is preferably a strip on which mirror surfaces and non-mirror surfaces are alternately arranged, or a strip in which white and black regions are alternately arranged. When the rotation rate detector 18 employs a Hall element, the member 22 to be detected is preferably a plurality of permanent magnets arranged equi-distantly on the circumference of the bottom surface of the turntable 8. On the upper surface of the turntable 8 is detachably mounted an object 24 to be inspected such as, for example, a semiconductor wafer or an original disk, e.g., an optical video disk on which no information is recorded. Air passages are formed in the turntable shaft 10 and the bearing 6 and are opened on the surfaces of the turntable 8 and the bearing 6. The passages are respectively coupled through a vacuum pipe 28 and solenoid valves 30 to a vacuum pump 32. A vacuum sensor 33 for detecting the operating state of the vacuum pump 32 is coupled with the vacuum pump 32. As shown in FIG. 3, the openings 26 of the passages are concentrically arranged on the turntable surface, the opening position corresponding to disks of various sizes to be mounted on the turntable 8.

Referring to FIG. 1, a support 36 having a bearing guide 34 is mounted on the base 4. An L-shaped arm 38 is movably supported by the bearing guide 34 of the support 36. An optical unit for detecting defects on the surface of the object 24 is provided on the arm 38. A laser unit 40, for example, an He-Ne laser unit and reflection mirrors 44, 46, 48 for optically coupling the optical head 42 to the laser unit 40 are also mounted on the arm 38. On the optical head 42 is mounted the first height sensor 50 for detecting the height of the optical head 42 from the surface of the disk to be inspected. The first height sensor 50 may preferably, be for example, a non-contact type microswitch which flows air toward the surface of the disk, and detects the pressure of the air flow, the non-contact microswitch being closed when the sensor 50 approaches the surface of the disk at a predetermined distance and detects the predetermined pressure. The optical head 42 is elevationally movably supported through a nut 52 by a feed shaft 54, which is connected to a motor 56, and the optical head 42 is elevationally moved by the motor 56. The second height sensor 58 is provided on the arm 38 in the vicinity of the feed shaft 54. This sensor 58 is closed, for example, when the optical head 42 of a limit switch reaches the maximum height limit from the surface of the disk and makes contact with the nut 52. A carriage 60 is further provided on the arm 38, and a feed shaft 62 passing through the carriage 60 is connected at one end thereof to a high speed motor 64 secured to the housing 2 and is also connected at the other end thereof through a solenoid clutch 66 to a low speed motor 68 secured to the housing 2. The motors 64, 68 are preferably of the reversibly rotatable type. The feed shaft 62 is rotated by either of the motors 64, 68, and hence the carriage 60 is moved in the axial direction of the feed shaft 62. Accordingly, the arm 38 moves on the bearing 34 in the longitudinal direction of the support 36, and the optical head 42 is thus moved in the radial direction of the disk 24. A position sensor 70, e.g., a linear potentiometer is provided in the support 36 for detecting the longitudinal position of the arm 38. Further, the motor 64 or 68 is engaged to move the carriage 60 so as to remove the optical head 42 from the surface of the turntable 8 when the disk 24 is mounted on the turntable 8. A limit switch 72 is provided at the moving limit point of the carriage 60 for detecting the removal of the optical head 42 from the turntable 8 when the carriage 60 reaches the moving limit, and the optical head 42 is stopped in response to a movement stop signal from the limit switch 72.

A keyboard panel 74 is provided on the front surface of the housing 2 for instructing the system, and a door 76 is hinged on the housing 2. A locking mechanism 80 for locking the door 76 is provided in the housing 2 and a lock sensor, for example, a limit switch 82 for sensing the door being in the locked condition, is provided in the vicinity of the locking mechanism.

The system shown in FIGS. 1 and 2 will be described further with reference to the block diagram shown in FIG. 3. The optical head 42 to which a laser beam is directed from the laser unit 40 is moved in the radial direction of the turntable 8 by a linear actuator 84, and is moved in the vertical direction which is normal to the turntable surface by a vertical actuator 86. The linear actuator 84 is comprised of the carriage 60, the feed shaft 62, the high speed motor 64, the solenoid clutch 66 and the low speed motor 68 and so forth, which were described hereinabove. The vertical actuator 86 is also comprised of the feed shaft 54, and the motor 56, and so forth, which were described hereinabove. Motor controllers (not shown) for controlling the motors 64, 68, 56 of the linear and vertical actuators 84, 86 are connected to a sequence control unit 88 provided under the keyboard panel 74 to control the motors 64, 68, 56 in accordance with instruction signals from the sequence control unit 88. The sensors 50, 58, 72 provided at the linear and vertical actuators 84, 86 are connected to the sequence control unit 88, and supply signals representing that the optical head 42 reaches the highest limit or the proximity height limit and that the optical head 42 is removed from the surface of the turntable 8 to the sequence control unit 88. The radial position of the optical head 42, which is moved by the linear actuator 84, is detected by a position sensor 70, which applies a position signal to a data processing unit 90, which will be hereinafter described in detail. When the size of the disk 24 to be placed on the turntable 8 is designated on the operation panel 74, the sequence control unit 88 produces operation signals for operating valve actuators 92 corresponding to the disk size. Accordingly, the designated solenoid valves 30 are opened by the valve actuators 92, the passage communicated with the opening 26 opened in the circumference of the surface of the turntable 8 corresponding to the disk size is coupled with the vacuum pump 32, and the disk 24 mounted on the turntable 8 is attracted and intimately contacted on the turntable 8. The rotating speed of the turntable 8 is designated on the keyboard panel 74, and the sequence control unit 88 produces an instruction signal correspnding to the prescribed rotating speed thus designated to a motor controller 94. The motor controller 94 controls the motor 12 in accordance with the given instruction signal, and rotates the turntable 8 at the prescribed rotating speed by the motor 12. The rotating speed of the turntable 8 is detected by the rotation rate detector 18, which supplies the detection signal to the sequence control unit 88, which thus compares it with the designated rotating speed. When the sequence control unit 88 supplies a stop signal to the brake unit 16, it will stop the rotation of the motor 12, and when the sequence control unit 88 supplies a start signal to the brake unit 16, it will release the stopping state of the motor 12 by the brake unit 16, thereby starting to rotate the motor 12.

The optical head 42 has, as shown in FIG. 4, a concave lens 96 for diverging a laser beam introduced via the mirror 48 and a collimator lens 98 for converting the diverged laser beam into a parallel laser beam. The parallel laser beam from the collimator lens 98 is transmitted through a beam splitter 100 and is directed through a quarter-wave plate 102 into an objective lens 104. The parallel laser beam is then converted via the objective lens 104, and is thus focused on the disk 24 to be inspected. The diverged laser beam thus reflected from the disk 24 is again converted into a parallel laser beam by the objective lens 104, and is passed through the quarter-wave plate 102 and into the beam splitter 100. Since the reflected parallel laser beam incident on the beam splitter 100 is delayed in a phase of 90° with respect to the incident parallel laser beam transmitted through the beam splitter 100 to the quarter-wave plate 102, the reflected parallel laser beam is reflected in the beam splitter 100, and is projected to the photo detector 110 of a defect signal generator 108 through a cylindrical lens 106 having different lateral and longitudinal magnifications. This photo detector 110 has four photo detecting regions each having an equal area radially divided. Each region generates a photo-electric signal having a level corresponding to the shape of the optical spot projected on the photo detector 110. The four photo-electric signals generated from the photo detector 110 of the defect signal generator 108 are supplied to a focus servo unit 112, which compares the four photoelectric signals and supplies the compared results to the sequence control unit 88. When the focal point of the objective lens 104 is not located on the surface of the disk 24 with the compared results, the sequence control unit 88 supplies an instruction signal to the vertical actuator 86 to move the optical head 42. After the focal point of the objective lens 104 is located on the surface of the disk 24, a driving mechanism (not shown) in the focus servo unit 112 is operated in accordance with the compared results from the focus servo unit 112 to move the objective lens 104 on its optical axis. When the focal point of the objective lens 104 is correctly positioned on the disk 24, the objective lens 104 is retained at the position by the focus servo unit 112. The focus servo unit 112 is operated to constantly locate the focal point of the objective lens 104 on the surface of the disk 24 during the inspection of the disk 24. The focus servo unit 112 is disclosed in detail in U.S. Pat. No. 4,079,247 of Bricot et al issued on Mar. 14, 1978.

Figure 6:
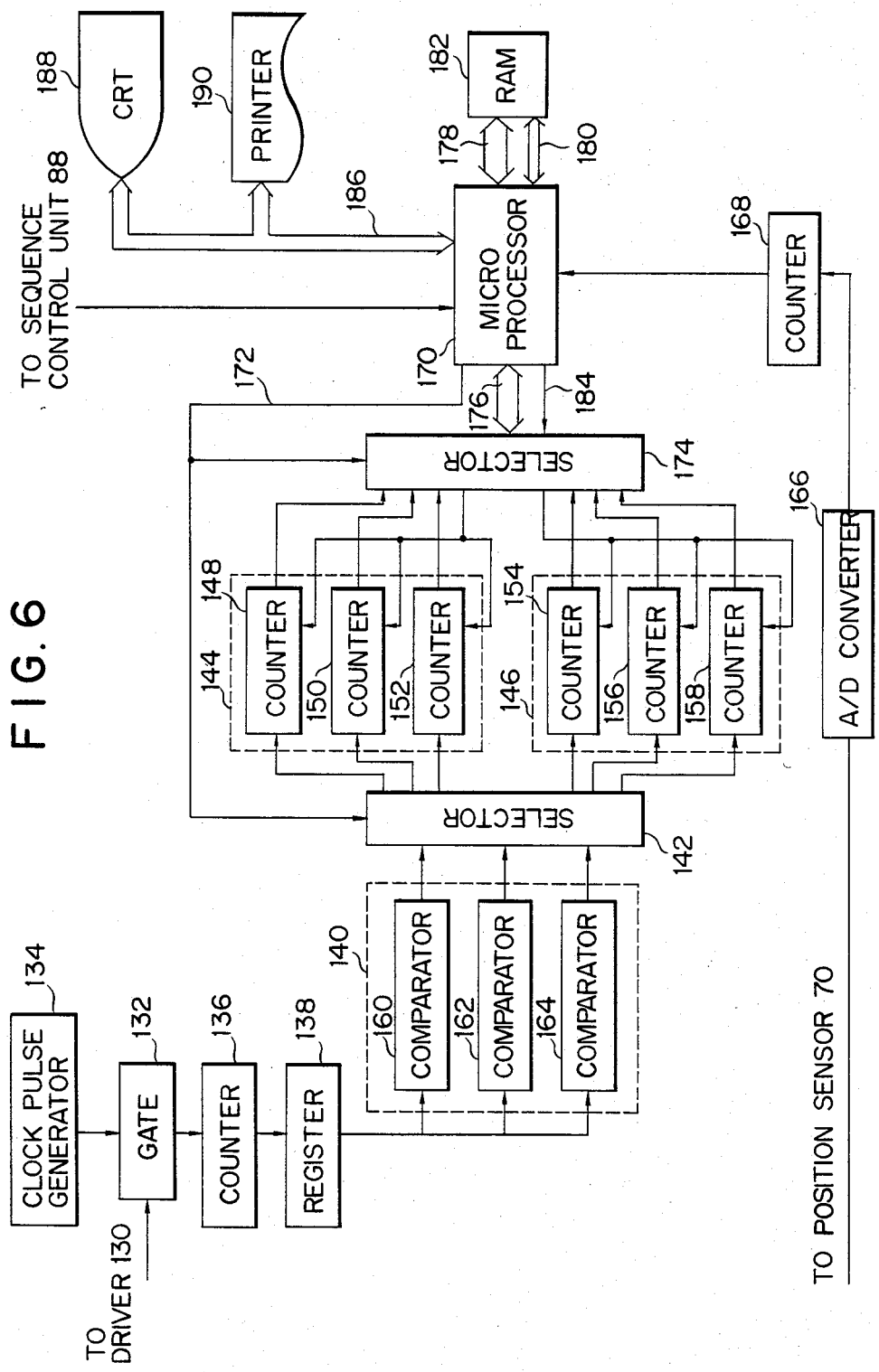
FIG. 6 is a block diagram showing the data processing unit shown in FIG. 3.

The circuits of the defect signal generator 108 and the data processing unit 90 are shown in FIGS. 5 and 6, respectively. The four photo-electric signals from the photo detector 110 are respectively amplified via pre-amplifiers 116, 118, 120, 122, and are then added by an adder 124. The level of the added signal corresponds to the intensity of the light beam reflected from the disk 24. The added signal is supplied to a base line correction circuit 126, the variation with time of the base line voltage is removed from the added signal, and the corrected added signal is supplied to a comparator 128. A reference voltage Vref having a prescribed threshold level is supplied to the comparator 128, which thus generates a defect signal as a pulse. The reference voltage Vref corresponds to a voltage level obtained by photo-electrically converting the light beam reflected on the optically flat region having no defect at all on the disk 24 into a photo-electric signal via the photo detector 110, amplifying the signal via the preamplifiers 115, 119, 120, 122 and adding them via the adder 124. When the laser beam is projected onto a defect on the disk 24 in a certain region, the comparator 128 generates a high level defect signal. When the laser beam is projected onto a region in which no defect is present on the disk 24, the comparator 128 generates a low level non-defect signal. That is, the comparator 128 supplied a pulse signal having a width corresponding to the length of the defect to a driver 130. This pulse signal is amplified by the driver 130, and is supplied to the gate 132 of the data processing unit 90, to which clock pulses are supplied from a clock pulse generator 134, as shown in FIG. 6. This gate 132 is opened when the high level defect signal is supplied from the driver 130 thereto, and the clock pulses are supplied through the gate 132 to a counter 136, which thus counts the clock pulses. This gate 132 is closed when the low level non-defect signal is supplied from the driver 130 thereto, and the clock pulses are not supplied to the counter 136. Accordingly, the counted value of the counter 136 corresponds to the pulse width of the defect signal, and thus means corresponds to the length of the defect. The counted value is temporarily stored in a register 138, and the consecutive counted values are classified into large, middle and small values by a magnitude comparator unit 140, and count up any of counters 148, 150, 152 or 154, 156, 158 in one of counter groups 144, 146 designated by a selector 142. More particularly, when a long defect is detected by the laser beam, the counted values are compared by three comparators 160, 162, 164 of the magnitude comparator unit 140, and a high level signal is generated merely from the first comparator 160. When the selector 142 selects the counter group 144, the comparators 160, 162, 164 are respectively connected to the counters 148, 150, 152, and the counter 148 is counted up by the high level signal from the comparator 160. When a short defect is detected by the laser beam, the counted values are compared by the three comparators 160, 162, 164, and a high level signal is generated as a small size defect signal only from the third comparator 164. Accordingly, only the counter 152 is counted up. When a middle size defect is detected by the laser beam in the same manner, a high level signal is generated only from the second comparator 162, and only the counter 150 is counted up. When a certain region on the surface of the disk 24 is, for example, helically scanned with the laser beam on the regions $a_0$ to $a_1$ on the circumference as will be hereinafter described, large, middle and small size defects are counted by the counters 148, 150, 152, respectively. The position of the laser beam spot on the disk 24 to which the laser beam is projected from the optical head is detected, by the position sensor 70, which in turn sends a position signal to the A/D converter 166 of the data processing unit 90 to convert it into a digital position signal. This digital position signal is counted by a counter 168, and when the counted value reaches a prescribed value, the counter 168 sends to a micro processor 170 a write signal representing that the prescribed regions $a_0$ to $a_1$ on the disk 24 are completely inspected. When a write signal is supplied to the micro processor 170, the micro processor 170 will supply a select signal to a line 172, thereby switching the selector 140 and the selector 174. Accordingly, the comparators 160, 162, 164 are disconnected from the counters 148, 150, 152 of the first counter group 144, and are connected to the counters 154, 156, 158 of the second counter group 146. Thus, the micro processor 170 is disconnected from the counters 154, 156, 158 of the second counter group 146 through a data bus 176, and is connected to the counters 148, 150, 152 of the first counter group 144. Accordingly, after the select signal is generated, the large, middle and small size signal is generated, the large, middle and small size signals are respectively supplied from the comparators 160, 162, 164 to the counters 154, 156, 158, which thus start counting of the signals. When a write signal is generated from the counter 168, the micro processor 170 supplies an address to an address bus 180, and the counted values of the counters 148, 150, 152 are sequentially loaded or written in the addresses of a RAM 182 through the data bus 176, the micro processor 170 and the data bus 178. When the counted values of the counters 148, 150, 152 are written in the prescribed addresses of the RAM 182, the micro processor 170 will supply a clear signal to a control line 184, and the clear signal is then supplied through the selector 174 to the counters 148, 150, 152 to clear the counters 148, 150, 152. When the predetermined region on the disk 24 is inspected by the laser beam again, the counter 168 will generate an end signal, the micro processor 170 will supply a select signal to the line 172, thereby switching the selectors 142, 174, and a similar operation as described above is repeated in the same manner.

After all the regions of the disk 24 are inspected by the laser beam, the defect data stored in the RAM 182 are read out by the micro processor 170, are transferred through a bus 186 to a CRT 188 or a printer 190, and are thus indicated on the CRT 188 or printed out by the printer 190.

The operation of the system will be described with reference to FIGS. 7 through 10 so as to described the sequence control unit 88 shown in FIG. 3.

When a power source is OFF, the brake unit 16 is retained in the state of braking, and the motor 12 stopped. The door 76 is locked by a locking mechanism 80.

Figure 7:
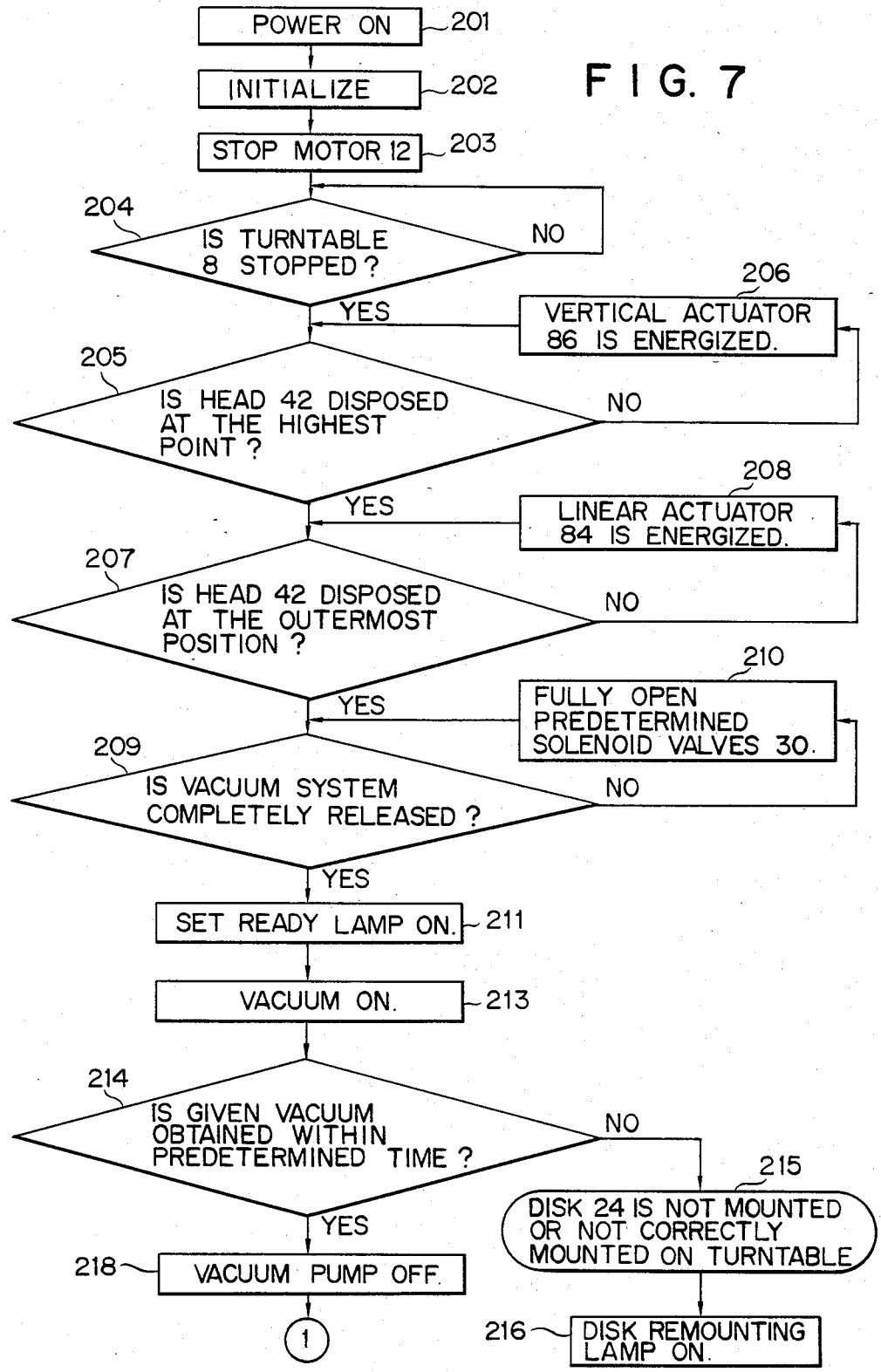
Figure 8:
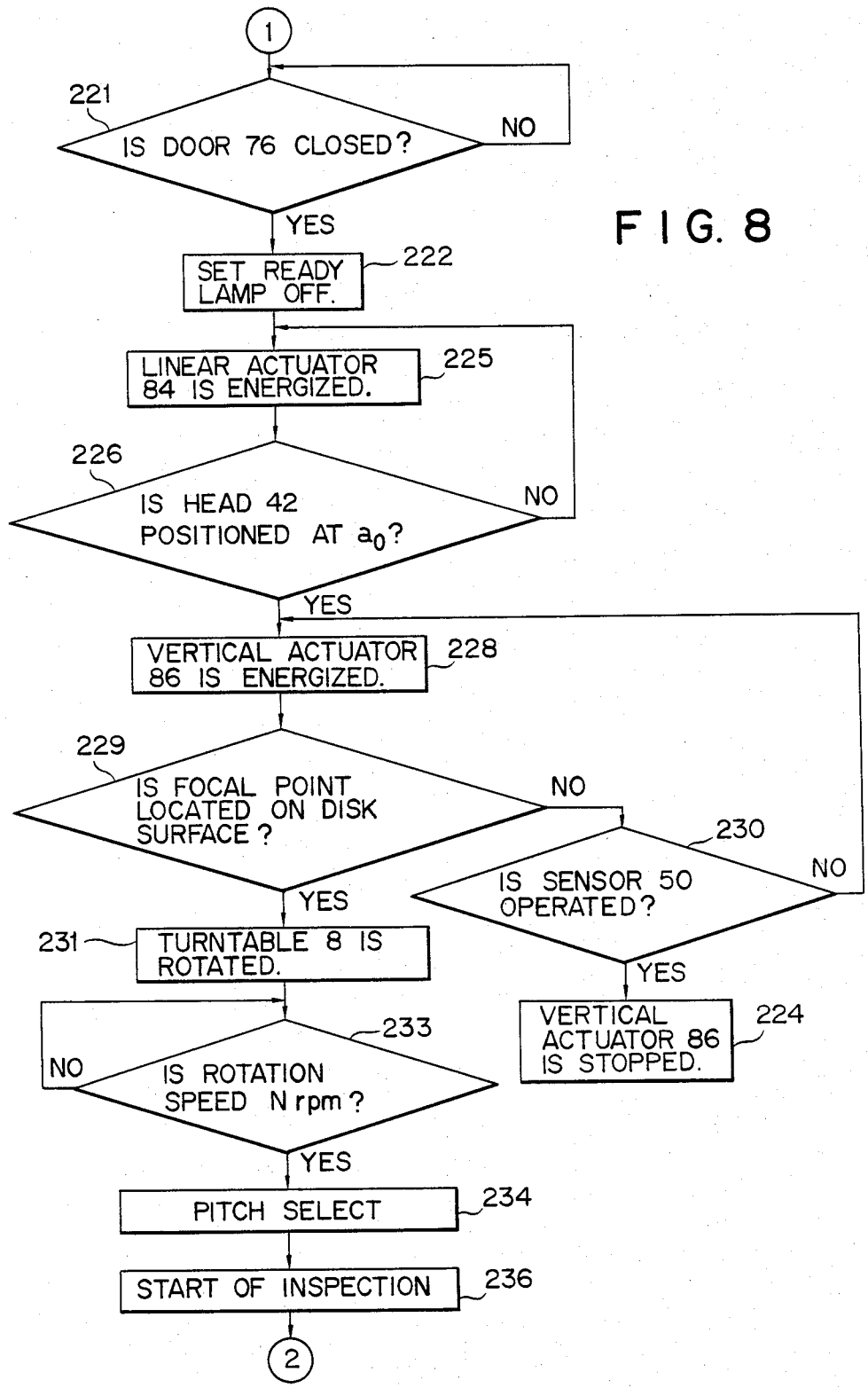
Figure 9:
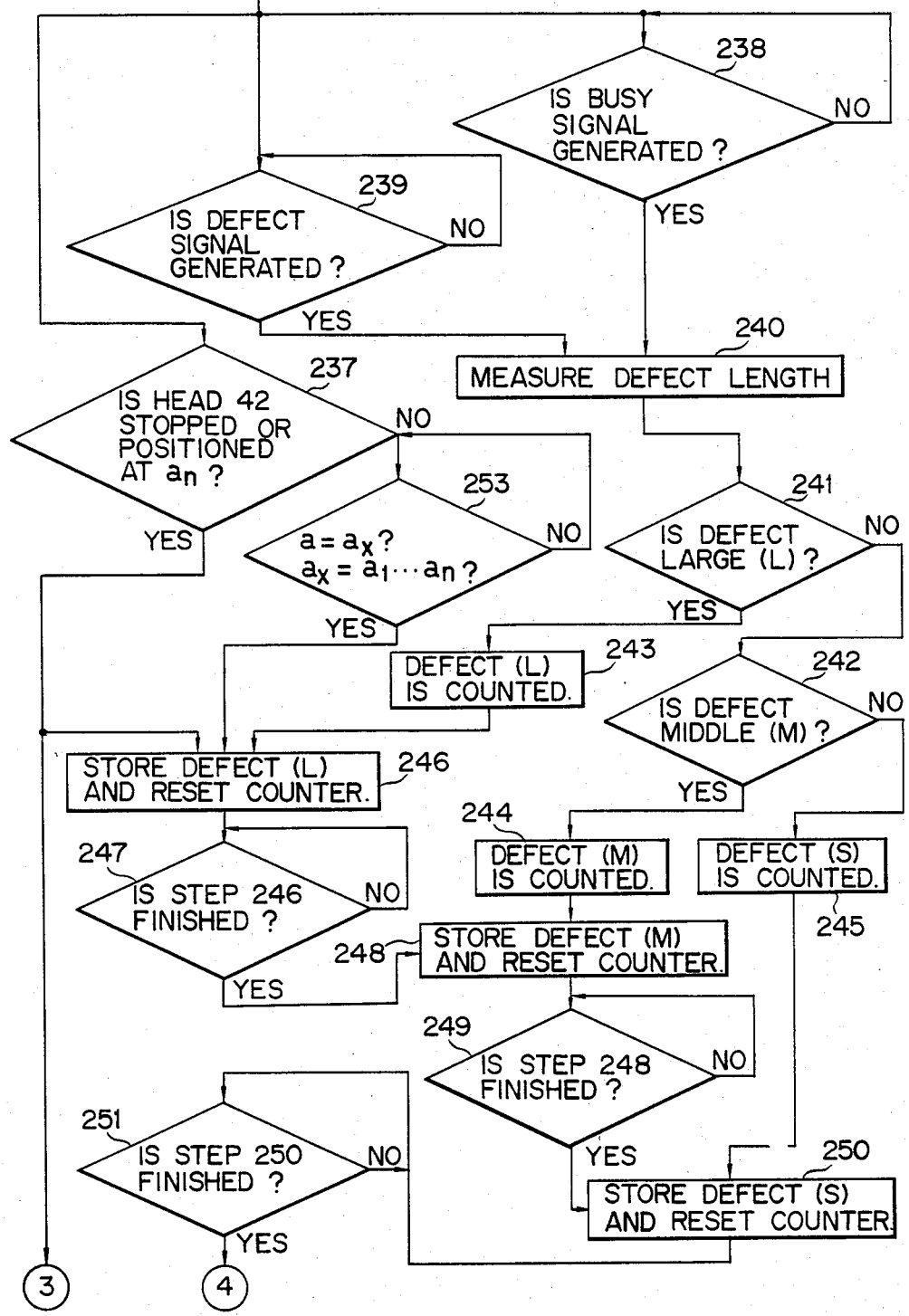

As shown in FIG. 7, when the power source is turned on in the step 201, a DC voltage is supplied to the laser unit 40 and the vacuum pump 32 to operate the system. When an initialization is executed in the step 202, the brake unit 16 continues to stop the drive motor 12 through the transmission or the belt 141 in the step 203. In the next step 204, the stop condition of the drive motor 12 and the turntable 8 is judged by the sequence control unit 88, which detects the signal from the rotation rate detector 18. When "YES" is generated in the step 204, the next step 205 will judge whether the optical head 42 is located at the highest position from the surface of the turntable 8 or not in accordance with the signal from the height limit sensor 58. When "NO" is generated in the step 205, the vertical actuator 86 is then operated in the next step 206, and the motor 56 will be driven to raise the optical head 42 to separate from the surface of the turntable 8. When "YES" is thus generated in the step 205, the next step 207 will judge whether the optical head 42 is located outside of the turntable 8 with a signal from the limit switch 72. When "NO" is generated in the step 207, the linear actuator 86 is then operated in the next step 208. In this case, the solenoid clutch 66 is disconnected, and only the high speed motor 64 is driven, thereby linearly moving the optical head 42 to close the limit switch 72. When "YES" is thus generated in the step 207, the step 209 will judge whether the vacuum evacuating system is opened or not and hence whether the vacuum pump 32 is operated or not. When "NO" is generated in the step 207, the predetermined solenoid valves 30 are fully opened in the next step 210. Thus, the initialization sequence is completed.

After this sequence is completed, the step 211 is executed to release the lock of the door 76 by the door locking mechanism 80, and the door 76 becomes openable. After the door 76 is opened, the disk 24 is mounted on the turntable 8. Then, the operation becomes "VACUUM ON" in the next step 213, the vacuum pump 32 is operated to vacuum the passage in the turntable shaft 10 and the bearing 6. Thus, the air in the space between the surface of the turntable 8 and the disk 24 is evacuated through the opening 26 confronted with the disk 24 within a predetermined time. The solenoid valves 30 is switched to be closed after evacuation. The evacuated state is judged in accordance with a vacuum signal from the vacuum sensor 38 in the next step 214. When "YES" is generated in the step 214, i.e., when the disk 24 is mounted at the correct position on the turntable 8, attracted to be held, and is prevented from being readily removed indiscreetly from the turntable 8, "VACUUM PUMP OFF" for stopping the operation of the vacuum pump 32 is executed in the next step 218. When "NO" is generated in the step 214, this means that the disk 24 is not correctly mounted on the turntable 8 or the disk is not mounted on the turntable 8. Accordingly, a disk remounting lamp is energized and it is necessary to remount the disk 24 or to mount it.

When the step 218 is finished, a door lamp is energized to instruct the operator to close the door 76. When the operator closes the door 76, in the step 221 the unit 88 will judge whether the door 76 is closed or not in accordance with a signal from the limit switch 82, the door locking mechanism 80 is operated according to the judged result, and the door 76 is locked. Subsequently, the door 76 is prevented from being opened until the operation is transferred to the next initialization step to energize the set ready lamp in the step 211, thereby securing the safety of the operation. When "YES" is generated in the step 221, the set ready lamp is deenergized in the next step 222, the operation then becomes "LOCATION READY" state, and the sequence control unit 88 advances to "LOCATION ON" state.

Figures 11, 12:
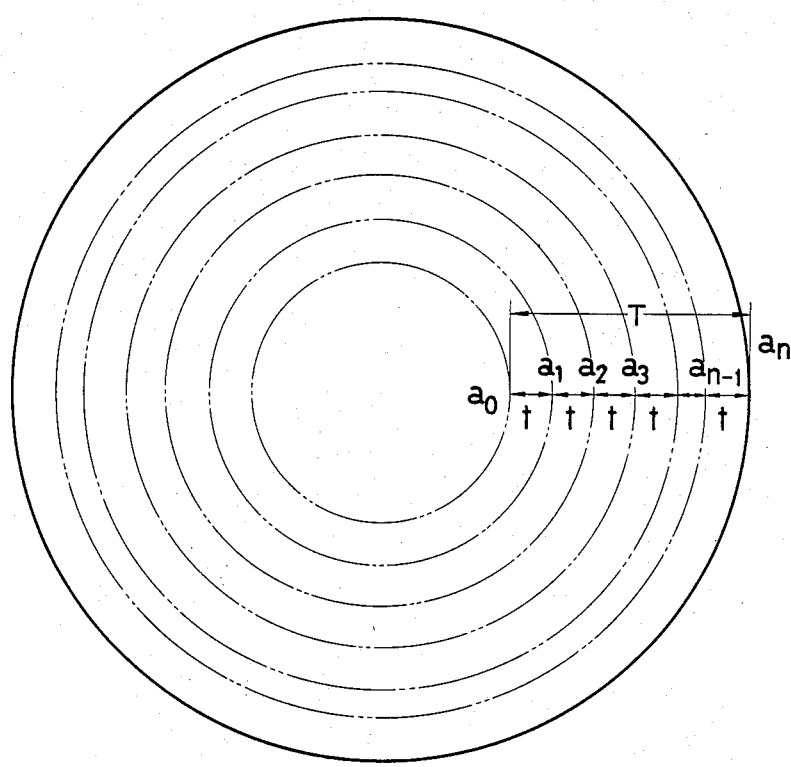
FIG. 11 is a plan view showing the inspecting region on the disk to be inspected shown in FIGS. 1 to 4.
FIG. 12 is a memory map showing the relationship between memory locations designated by addresses in a RAM shown in FIG. 6 and the inspection regions shown in FIG. 11.

A signal is inputted to the linear actuator 84 in the next step 225. Thus, the high speed motor 64 is driven to move the optical head 42 to the center area of the turntable 8. The inspecting region T of the disk 24 is defined, from the inner peripheral end $a_0$ of the center area to the outer peripheral end $a_n$, as shown in FIG. 11. The optical axis of the objective lens 104 of the optical head 42 is moved to the position of the inspection starting point $a_0$ and is stopped there. More particularly, when the optical axis is moved to the vicinity of the inspection starting point $a_0$. The high speed motor 64 is deenergized and the solenoid clutch 66 is operated to connect the feed shaft 62 to the low speed motor 68 in accordance with the position signal from the position sensor 70. The motor 68 is driven, the optical head 42 is thus fed at low speed, and the optical axis of the objective lens 104 is finely positioned at the inspection starting point $a_0$. In the step 226, it is judged whether the optical axis of the objective lens 104 reaches the inspection starting point $a_0$ or not in accordance with the position signal from the position sensor 70. When "YES" is generated in the step 226, the sequence control unit 88 becomes "HEIGHT READY" state. Then, in the next step 228, the "HEIGHT ADJUST ON" signal is outputted to the vertical actuator 86. Thus, the motor 56 is driven to approach the optical head 42 to the turntable 8. When the optical head 42 is thus lowered, the objective lens 104 is focused on the surface of the disk 24. Thereafter, the photo-electric signal from the photo detector is supplied to the focus servo unit 112, which in turn drives the objective lens 104, which is thus focused accurately at the focal point on the surface of the disk 24. This focusing operation is carried out in the step 229. When the focus signal is not outputted due to a fault in the step 229, i.e., when "NO" is generated in the step 229, it is advanced to the next step 230. In the step 230, the height sensor 50 is operated. When the optical head 42 is too close approached to the disk 24, the vertical actuator 85 is stopped in accordance with the detection signal from the sensor 50 in the step 224. Accordingly, the optical head can be automatically focused on the disk 42 by the aforementioned operation, and it can prevent the collision of the optical head 24 on the disk 24 by the stop of the vertical actuator 86 in accordance with the signal from the sensor 50.

When "YES" is generated in the step 229, the sequence control unit 88 becomes in the "ROTATION READY" state. After the "ROTATION READY" state, a brake release signal is fed to the brake unit 16, and a "ROTATION ON" signal is fed to the motor controller. Accordingly, the motor 12 of the driving mechanism 11 is driven, and the turntable 8 starts rotating. Thereafter, it is advanced to the next step 233. In the step 233, it is judged whether the turntable 8 reaches its predetermined rotating speed (N rpm) or not in accordance with the output signal from the rotation rate detector 18. When "YES" is generated in the step 233, the sequence control unit 88 produces a feed pitch signal for instructing the feed pitch of the optical head 42 in the step 234 shown in FIG. 9 to the linear actuator 84, and becomes in the "TEST READY" state. When the "TEST READY" signal is thus applied to the sequence control unit 88, it is advanced to the next step 236 to start inspecting of the disk.

When the disk is inspected, the sequence control unit 88 supplies a "TEST BUSY" signal to the data processing unit 90. Thus, the data processing unit 90 detects the start of the inspection in accordance with the TEST BUSY signal in the step 238, thereby becoming ready to receive defect signals outputted from the defect signal generator 108. While the TEST BUSY signal is ordinarily outputted, it is fed to the linear actuator 84 continuously, a voltage for moving the optical head 42 at a prescribed speed is thus continuously supplied to the low speed motor 68 of the linear actuator 84 and the optical head 42 is moved at the prescribed speed toward the outer peripheral direction of the disk 24. Accordingly, the surface of the disk 24 is spirally scanned by the laser beam emitted from the optical head 42, and any defect on the surface of the disk is detected by this scanning operation.

More particularly, in the step 239, the laser beam projected from the optical head 42 is regularly reflected when no defect exists on the surface of the disk 24 to be inspected, and is thus incident into the generator 108 for photo-electrically converting it. When the laser beam is projected on a defect of the surface of the disk 24, it is scattered, and the intensity of the laser beam is reduced. The defect on the surface of the disk can be detected in accordance with the variation in the intensity of the reflected laser beam. The detected electrical signal corresponding to the variation in the intensity of the reflected laser beam is amplified in the defect signal generator 108, is compared with a predetermined reference voltage Vref, and is thus converted into a pulse signal and the pulse signal is then outputted as defect information to the data processing unit 90. The defect information thus received at the data processing unit 90 is measured in length in step 240, and is then processed in the following steps 241 and 242. In the steps 241, 242, the defect information measured in the length by the magnitude comparator unit 140 is classified into large (L), middle (M) and small (S) classes in accordance with the lengths. The compared results are sequentially counted by the counters 148, 150, 152 or 154, 156, 158 in the respective classes in the steps 243, 244 and 245. On the other hand, the TEST BUSY signal is received, and the step 237 is carried out. In the step 237, it is judged whether the optical head 42 reaches the inspection ending point $a_n$ or not. When the optical head 42 reaches the point $a_n$, "YES" is generated in accordance with the END signal outputted from the position sensor 70 or with the STOP signal outputted under the prescribed conditions. When "NO" is generated in the step 237, it is advanced to the next step 253. In the step 253, the inspecting region T is divided into a plurality of small inspecting region segments t, . . . , and it is judged that the optical head is located at the boundary points $a_1$, $a_2$, $a_3$, . . . predetermined in accordance with the position signals from the position sensor 70. When the optical head is detected in the respective small inspecting region segments in the step 253, it is advanced to the next step 246 every time "YES" is generated in the step 253 or every time the judgement in the step 237 becomes "YES". In the step 246, the defect information of the large class (L) counted in the step 243 is stored in the address designated in the RAM 182 in accordance with the position signal from the position sensor 70, and the counter 148 or 154 is reset. In the step 247, it is judged whether the operation of the step 246 is finished or not. When "YES" is generated in the step 247, the system advances to the next step 248. In the step 248, the defect information of the middle class (M) counted in the step 244 is stored in the address differently assigned in the RAM 182 from the above memory location, and the counter 150 or 156 is reset. In the step 248, it is judged whether the operation of the step 247 is finished or not. When "YES" is generated in the step 248, the system advances to the next step 250. In this step 250, defect information of the small class (S) counted in the step 245 is stored in the address differently designated in the RAM 182 from the above memory locations of two types, and the counter 152 or 158 is reset. In the step 251, it is judged whether the operation of the step 250 is finished or not. More particularly, the above described processes are repeated every time the small inspecting region segments t, . . . are completely scanned, and the completion of the operation of the step 250 is judged.

FIG. 12 shows an example of the locations of the addresses in which the defect information is stored in which the reference characters L, M, S represent respectively the classes of the length of the defect information. When the disk is scanned to the inspection ending point $a_n$, the END signal is outputted from the position sensor 70. When "YES" is generated in the step 237, i.e., the END signal or the STOP signal is outputted. When the judgement in the step 251 becomes "YES", the system advances to the step 252. In the step 252, data is processed to enable the indication on the display unit, for example, the hard copy and CRT. The display units F and G indicate the defect information stored in the step 253 in an arbitrary display format. It is judged whether the display is finished or not in the step 254. When "YES" is generated in the step 254, or the judgement in the step 252 becomes "YES", the sequence control unit 88 receives the signal, and it advances to the END. The TEST BUSY state is released, and the completion of the inspection is displayed.

After the completion of the inspection, in order to exchange the disk 24, the operations in the steps 202 for the initialization to 211 are carried out, the door 76 is opened, the inspected disk 24 is removed from the turntable 8, and then a new disk 24 to be inspected is mounted on the turntable 8.

It is noted that the foregoing description is directed to one preferred embodiment of the system for inspecting defects on an optical plane, but the present invention is not limited only to this embodiment.

For instance, the address of the data processing unit may be generated in accordance with the position signal from the rotation rate detector 18. In this case, the member 22 to be detected, e.g., one of the stripes 22 may be, for example, formed different in size from the other, thereby providing a reference point for the detection of the rotating angle.

Then, the above assignment of the address may be executed in accordance with the position signals from the respective positon sensor 70 and rotation rate detector 18, thereby accurately identifying the property of the distribution of the defect information.

It is noted that the data processing unit 90 may be provided to apply the signal enabling the intermittent feeding at the feed controlling time or the feeding of only the arbitrary inspecting region to the sequence control unit 88.

Further, the aforementioned class indentifying circuit for classifying the defect information may not always be necessary, but the defect inrormation corresponding to a defect having a size larger than a predetermined length (size) may be handled as one type of defect information irrespective of the classes of the defect information having the predetermined length (size) and may be stored in the RAM.

In addition, it is noted that in the execution of the present invention, the turntable, the table driving mechanism, the detecting system, the laser beam generator, the optical head, the detecting system moving mechanism, the moving amount detecting means, the signal processing unit, the data processing unit, the sequence control unit, and so forth may also be modified in specific structure, shape, position and relatively coupling relation, etc. within the spirit and scope of the present invention.

It is appreciated from the foregoing description that since the system of the present invention is constructed to have the turntable, the table driving mechanism, the optical head, the optical head moving mechanism, the position sensor, the defect signal generator, and the data processing unit, and so forth and to operate them in a predetermined inspecting sequence in accordance with the instructions from the sequence control unit, the inspecting work can be automatically executed without visual inspection, and can also be efficiently performed to detect surface defects of the object to be inspected.

It is also understood that since the system of the present invention is constructed to employ a laser beam for detection of surface defects, to readily obtain the parallel laser beam of the fine spot and to provide a remarkable difference between the scattered (or diffracted) laser beam due to the existence of the surface defect and the non-scattered beam, it can detect a smaller surface defect with higher reliability.

Further, it is also appreciated that since the system of the present invention is operated to store the surface defect in the prescribed memory location the address of which is assigned in accordance with the position signal from the moving amount detecting means by the process in the data processing unit and the defect signal generator, the surface defect can be quantitatively formed.

What we claim is:

1. A system for detecting defects on an optically flat surface of an object to be inspected, comprising:
   a turntable having a surface on which the object is mounted;
   means for rotating said turntable;
   means for generating a laser beam;
   an optical unit for projecting said generated laser beam onto said optically flat surface of the object and directing the laser beam reflected from said optically flat surface in a predetermined direction, said optical unit including an objective lens for converging the laser beam, and means for always locating the focal point of the objective lens on said pivotally flat surface of the object;
   means for converting the reflected laser beam directed by said optical unit into a photo-electric signal;
   means for moving said optical unit relative to said turntable in a radial direction of said turntable;
   means responsive to the position of said object and for generating a position signal depending on the position of said object onto which said laser beam is projected;
   means responsive to said photo-electric signal and for generating a defect signal as a function of said photoelectric signal;
   means responsive to the duration of said defect signal for detecting the length of a detected defect in said optically flat surface of said object being inspected;
   means responsive to said position signal for generating addresses as a function of said position signal, said address generating means including memory means having a number of memory locations for storing said defect signals in the locations designated by the generated addresses; and
   means for activating the aforesaid respective means in a predetermined sequence.

2. The system according to claim 1, wherein said memory means includes means for classifying the length of the detected defects on said surface of said object, on the basis of said defect signal, into a plurality of classes and stores the defects classified in the classes in the addresses designated by the addresses of the classes.

3. The system according to claim 1, wherein said means responsive to the duration of said defect signal comprises gate means which is activated to open and close responsive to said defect signal.

4. The system according to claim 3, wherein said memory means includes means responsive to the detected length of a detected defect for storing information corresponding to said detected length.

5. The system according to claim 1, wherein said memory means includes means responsive to the detected length of a detected defect for storing information corresponding to said detected length.

6. The system according to claim 1, wherein said system further comprises means for moving said optical unit in a vertical direction normal to the surface of the turntable.

7. The system according to claim 1, wherein said system further comprises means for attracting the object onto the surface of said turntable.

8. The system according to claim 1, wherein said system further comprises means for detecting the rotating speed of said turntable.

9. The system according to claim 1, wherein said system further comprises means for reading out the defect information stored in said memory means.

* * * * *